US010555805B2

(12) United States Patent
Lang et al.

(10) Patent No.: US 10,555,805 B2
(45) Date of Patent: Feb. 11, 2020

(54) ANTERIOR CORNEAL SHAPES AND METHODS OF PROVIDING THE SHAPES

(71) Applicant: RVO 2.0, Inc., Aliso Viejo, CA (US)

(72) Inventors: Alan Lang, Long Beach, CA (US); Keith Holliday, Lake Forest, CA (US)

(73) Assignee: RVO 2.0, Inc., Aliso Viejo, CA (US)

( * ) Notice: Subject to any disclaimer, the term of this patent is extended or adjusted under 35 U.S.C. 154(b) by 0 days.

(21) Appl. No.: 14/217,056

(22) Filed: Mar. 17, 2014

(65) Prior Publication Data
US 2014/0200665 A1 Jul. 17, 2014

Related U.S. Application Data

(63) Continuation-in-part of application No. 12/877,799, filed on Sep. 8, 2010, and a continuation-in-part of application No. 12/418,325, filed on Apr. 3, 2009, now Pat. No. 8,900,296, which is a continuation-in-part of application No. 11/738,349, filed on Apr. 20, 2007, said application No. 11/554,544 is a continuation-in-part of application No. 11/554,544, filed on Oct. 30, 2006, now Pat. No. 8,057,541.

(60) Provisional application No. 61/799,847, filed on Mar. 15, 2013, provisional application No. 61/155,433, filed on Feb. 25, 2009, provisional application No. 61/042,659, filed on Apr. 4, 2008, provisional application No. 60/776,458, filed on Feb. 24, 2006.

(51) Int. Cl.
A61F 2/14 (2006.01)
A61F 9/008 (2006.01)

(52) U.S. Cl.
CPC .......... *A61F 2/147* (2013.01); *A61F 9/00834* (2013.01)

(58) Field of Classification Search
CPC .. A61F 2/14–2/1453; A61F 2250/0091; A61F 9/00834
See application file for complete search history.

(56) References Cited

U.S. PATENT DOCUMENTS

| 2,714,721 | A | 8/1955 | Stone, Jr. |
| 3,091,328 | A | 5/1963 | Leonardos |
| 3,168,100 | A | 2/1965 | Rich |
| 3,343,657 | A | 9/1967 | Speshyock |
| 3,379,200 | A | 4/1968 | Pennell |
| 3,482,906 | A | 12/1969 | Volk |
| 3,743,337 | A | 7/1973 | Crary |

(Continued)

FOREIGN PATENT DOCUMENTS

| DE | 3208729 A1 | 9/1983 |
| EP | 0308077 A2 | 3/1989 |

(Continued)

OTHER PUBLICATIONS

Spector, "Clinical Methods: The History, Physical, and Laboratory Examinations", Butterworth Publishers, 3$^{rd}$ Edition, Chapter 58, The Pupils, (1990).*

(Continued)

*Primary Examiner* — Paul B Prebilic
(74) *Attorney, Agent, or Firm* — Shay Glenn LLP

(57) ABSTRACT

Methods of treating presbyopia of an eye. A corneal inlay is inserted within the cornea such that the central thickness of the corneal inlay is 3 to 7 times a central elevation change.

11 Claims, 5 Drawing Sheets

(56) References Cited

U.S. PATENT DOCUMENTS

| | | |
|---|---|---|
| 3,770,113 A | 11/1973 | Thomas |
| 3,879,076 A | 4/1975 | Barnett |
| 3,950,315 A | 4/1976 | Cleaver |
| 3,996,627 A | 12/1976 | Deeg et al. |
| 4,030,480 A | 6/1977 | Meyer |
| 4,037,604 A | 7/1977 | Newkirk |
| 4,037,866 A | 7/1977 | Price |
| 4,039,827 A | 8/1977 | Zdrok et al. |
| 4,065,816 A | 1/1978 | Sawyer |
| 4,071,272 A | 1/1978 | Drdlik |
| 4,093,291 A | 6/1978 | Schurgin |
| 4,136,406 A | 1/1979 | Norris |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A | 3/1981 | Poler |
| 4,268,133 A | 5/1981 | Fischer et al. |
| 4,326,306 A | 4/1982 | Poler |
| 4,357,940 A | 11/1982 | Muller |
| 4,392,569 A | 7/1983 | Shoup |
| 4,418,991 A | 12/1983 | Breger |
| 4,423,809 A | 1/1984 | Mazzocco |
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A | 3/1985 | Burk |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A | 1/1986 | Koeniger |
| 4,573,998 A | 3/1986 | Mazzocco |
| 4,580,882 A | 4/1986 | Nuchman et al. |
| 4,586,929 A | 5/1986 | Binder |
| 4,604,087 A | 8/1986 | Joseph |
| 4,607,617 A | 8/1986 | Choyce |
| 4,616,910 A | 10/1986 | Klein |
| 4,618,227 A | 10/1986 | Bayshore |
| 4,619,256 A | 10/1986 | Horn |
| 4,624,664 A | 11/1986 | Peluso et al. |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,709,697 A | 12/1987 | Muller |
| 4,721,124 A | 1/1988 | Tuerkheimer et al. |
| 4,726,367 A | 2/1988 | Shoemaker |
| 4,750,901 A | 6/1988 | Molteno |
| 4,762,496 A | 8/1988 | Maloney et al. |
| 4,766,895 A | 8/1988 | Reynolds |
| 4,769,033 A | 9/1988 | Nordan |
| 4,772,283 A | 9/1988 | White |
| 4,778,462 A | 10/1988 | Grendahl |
| 4,798,609 A | 1/1989 | Grendahl |
| 4,806,382 A | 2/1989 | Goldberg et al. |
| 4,836,201 A | 6/1989 | Patton et al. |
| 4,840,175 A | 6/1989 | Peyman |
| 4,842,599 A | 6/1989 | Bronstein |
| 4,844,242 A | 7/1989 | Chen et al. |
| 4,851,003 A | 7/1989 | Lindstrom |
| 4,860,885 A | 8/1989 | Kaufman et al. |
| 4,865,552 A | 9/1989 | Maloney et al. |
| 4,886,488 A | 12/1989 | White |
| 4,888,016 A | 12/1989 | Langerman |
| 4,897,981 A | 2/1990 | Beck |
| 4,911,715 A | 3/1990 | Kelman |
| 4,919,130 A | 4/1990 | Stoy et al. |
| 4,923,467 A | 5/1990 | Thompson |
| 4,934,363 A | 6/1990 | Smith et al. |
| 4,936,825 A | 6/1990 | Ungerleider |
| 4,946,436 A | 8/1990 | Smith |
| 4,955,903 A | 9/1990 | Sulc et al. |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A | 5/1991 | Mercier |
| 5,022,414 A | 6/1991 | Muller |
| 5,030,230 A | 7/1991 | White |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,912 A | 6/1992 | Kaplan et al. |
| 5,123,921 A | 6/1992 | Werblin et al. |
| 5,139,518 A | 8/1992 | White |
| 5,166,712 A * | 11/1992 | Portney ............... 351/159.49 |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst et al. |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett et al. |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portney |
| 5,273,750 A | 12/1993 | Homiger et al. |
| 5,282,851 A | 2/1994 | Jacob-LaBarre |
| 5,300,020 A | 4/1994 | L'Esperance, Jr. |
| 5,300,116 A | 4/1994 | Chirila et al. |
| 5,312,413 A | 5/1994 | Eaton et al. |
| 5,318,044 A | 6/1994 | Kilmer et al. |
| 5,318,046 A | 6/1994 | Rozakis |
| 5,318,047 A | 6/1994 | Davenport et al. |
| 5,336,261 A | 8/1994 | Barrett et al. |
| 5,338,291 A | 8/1994 | Speckman et al. |
| 5,344,448 A | 9/1994 | Schneider et al. |
| 5,346,464 A | 9/1994 | Camras |
| 5,370,607 A | 12/1994 | Memmen |
| 5,372,577 A | 12/1994 | Ungerleider |
| 5,385,582 A | 1/1995 | Ommaya |
| 5,391,201 A * | 2/1995 | Barrett et al. ............ 623/5.12 |
| 5,397,300 A | 3/1995 | Baerveldt et al. |
| 5,405,384 A | 4/1995 | Silvestrini |
| 5,407,241 A | 4/1995 | Harrison |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,487,377 A | 1/1996 | Smith et al. |
| 5,489,301 A | 2/1996 | Barber |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,533,997 A | 7/1996 | Ruiz |
| 5,570,142 A | 10/1996 | Lieberman |
| 5,591,185 A | 1/1997 | Kilmer et al. |
| 5,598,234 A | 1/1997 | Blum et al. |

(56) References Cited

U.S. PATENT DOCUMENTS

| | | | |
|---|---|---|---|
| 5,616,148 A | 4/1997 | Eagles et al. |
| 5,620,450 A | 4/1997 | Eagles et al. |
| 5,628,794 A | 5/1997 | Lindstrom |
| 5,630,810 A | 5/1997 | Machat |
| 5,634,943 A | 6/1997 | Villain et al. |
| 5,643,276 A | 7/1997 | Zaleski |
| 5,647,865 A | 7/1997 | Swinger |
| 5,657,108 A | 8/1997 | Portney |
| 5,682,223 A | 10/1997 | Menezes et al. |
| 5,684,560 A | 11/1997 | Roffman et al. |
| 5,715,031 A | 2/1998 | Roffman et al. |
| 5,716,633 A | 2/1998 | Civerchia |
| 5,722,948 A | 3/1998 | Gross |
| 5,722,971 A | 3/1998 | Peyman |
| 5,728,155 A | 3/1998 | Anello et al. |
| 5,732,990 A | 3/1998 | Yavitz et al. |
| 5,752,928 A | 5/1998 | de Roulhac et al. |
| 5,755,785 A | 5/1998 | Rowsey et al. |
| 5,766,181 A | 6/1998 | Chambers et al. |
| 5,772,667 A | 6/1998 | Blake |
| 5,779,711 A | 7/1998 | Kritzinger et al. |
| 5,785,674 A | 7/1998 | Mateen |
| 5,800,442 A | 9/1998 | Wolf et al. |
| 5,800,529 A | 9/1998 | Brauker et al. |
| 5,805,260 A | 9/1998 | Roffman et al. |
| 5,810,833 A | 9/1998 | Brady et al. |
| 5,817,115 A | 10/1998 | Nigam |
| 5,824,086 A | 10/1998 | Silvestrini |
| 5,847,802 A | 12/1998 | Menezes et al. |
| 5,855,604 A | 1/1999 | Lee |
| 5,860,984 A | 1/1999 | Chambers et al. |
| 5,872,613 A | 2/1999 | Blum et al. |
| 5,873,889 A | 2/1999 | Chin |
| 5,876,439 A | 3/1999 | Lee |
| 5,888,243 A | 3/1999 | Silverstrini |
| 5,893,719 A | 4/1999 | Radow |
| 5,913,898 A | 6/1999 | Feingold |
| 5,919,185 A | 7/1999 | Peyman |
| 5,928,245 A | 7/1999 | Wolf et al. |
| 5,929,968 A | 7/1999 | Cotie et al. |
| 5,929,969 A | 7/1999 | Roffman |
| 5,935,140 A | 8/1999 | Buratto |
| 5,941,583 A | 8/1999 | Raimondi |
| 5,944,752 A | 8/1999 | Silvestrini |
| 5,945,498 A | 8/1999 | Hopken et al. |
| 5,964,748 A | 10/1999 | Peyman |
| 5,964,776 A | 10/1999 | Peyman |
| 5,968,065 A | 10/1999 | Chin |
| 5,976,150 A | 11/1999 | Copeland |
| 5,976,168 A | 11/1999 | Chin |
| 5,980,549 A | 11/1999 | Chin |
| 6,007,510 A | 12/1999 | Nigam |
| 6,010,510 A | 1/2000 | Brown et al. |
| 6,024,448 A | 2/2000 | Wu et al. |
| 6,033,395 A | 3/2000 | Peyman |
| 6,036,714 A | 3/2000 | Chin |
| 6,050,999 A | 4/2000 | Paraschac et al. |
| 6,055,990 A | 5/2000 | Thompson |
| 6,059,775 A | 5/2000 | Nielsen |
| 6,066,170 A | 5/2000 | Lee |
| 6,068,642 A | 5/2000 | Johnson et al. |
| 6,079,826 A | 6/2000 | Appleton et al. |
| 6,083,231 A | 7/2000 | Van Noy et al. |
| 6,086,202 A | 7/2000 | Chateau et al. |
| 6,090,141 A | 7/2000 | Lindstrom |
| 6,102,946 A * | 8/2000 | Nigam .................... A61F 2/147 623/5.15 |
| 6,110,166 A | 8/2000 | Juhasz et al. |
| 6,120,148 A | 9/2000 | Fiala et al. |
| 6,125,294 A | 9/2000 | Scholl et al. |
| 6,129,733 A | 10/2000 | Brady et al. |
| 6,139,560 A | 10/2000 | Kremer |
| 6,142,969 A | 11/2000 | Nigam |
| 6,143,001 A | 11/2000 | Brown et al. |
| 6,159,241 A | 12/2000 | Lee et al. |
| 6,171,324 B1 | 1/2001 | Cote et al. |
| 6,175,754 B1 | 1/2001 | Scholl et al. |
| RE37,071 E | 2/2001 | Gabrielian et al. |
| 6,183,513 B1 | 2/2001 | Guenthner et al. |
| 6,197,019 B1 | 3/2001 | Peyman |
| 6,197,057 B1 | 3/2001 | Peyman et al. |
| 6,197,058 B1 | 3/2001 | Portney |
| 6,203,538 B1 | 3/2001 | Peyman |
| 6,203,549 B1 | 3/2001 | Waldock |
| 6,203,557 B1 | 3/2001 | Chin |
| 6,206,919 B1 | 3/2001 | Lee |
| 6,210,005 B1 | 4/2001 | Portney |
| 6,214,015 B1 | 4/2001 | Reich et al. |
| 6,214,044 B1 | 4/2001 | Silverstrini |
| 6,217,571 B1 | 4/2001 | Peyman |
| 6,221,067 B1 | 4/2001 | Peyman |
| 6,228,113 B1 | 5/2001 | Kaufman |
| 6,228,114 B1 | 5/2001 | Lee |
| 6,248,111 B1 | 6/2001 | Glick et al. |
| 6,250,757 B1 | 6/2001 | Roffman et al. |
| 6,251,114 B1 | 6/2001 | Farmer et al. |
| 6,264,648 B1 | 7/2001 | Peyman |
| 6,264,670 B1 | 7/2001 | Chin |
| 6,264,692 B1 | 7/2001 | Woffinden et al. |
| 6,267,768 B1 | 7/2001 | Deacon et al. |
| 6,271,281 B1 | 8/2001 | Liao et al. |
| 6,277,137 B1 | 8/2001 | Chin |
| 6,280,449 B1 | 8/2001 | Blake |
| 6,280,470 B1 | 8/2001 | Peyman |
| 6,283,595 B1 | 9/2001 | Breger |
| 6,302,877 B1 | 10/2001 | Ruiz |
| 6,325,509 B1 | 12/2001 | Hodur et al. |
| 6,325,792 B1 | 12/2001 | Swinger et al. |
| 6,350,272 B1 | 2/2002 | Kawesch |
| 6,361,560 B1 | 3/2002 | Nigam |
| 6,364,483 B1 | 4/2002 | Grossinger et al. |
| 6,371,960 B2 | 4/2002 | Heyman et al. |
| 6,391,230 B1 | 5/2002 | Sarbadhikari |
| 6,398,277 B1 | 6/2002 | McDonald |
| 6,398,789 B1 | 6/2002 | Capetan |
| 6,428,572 B2 | 8/2002 | Nagai |
| 6,435,681 B2 | 8/2002 | Portney |
| 6,436,092 B1 | 8/2002 | Peyman |
| 6,447,519 B1 | 9/2002 | Brady et al. |
| 6,447,520 B1 | 9/2002 | Ott et al. |
| 6,458,141 B1 | 10/2002 | Peyman |
| 6,461,384 B1 | 10/2002 | Hoffmann et al. |
| 6,471,708 B2 | 10/2002 | Green |
| 6,474,814 B1 | 11/2002 | Griffin |
| 6,506,200 B1 | 1/2003 | Chin |
| 6,511,178 B1 | 1/2003 | Roffman et al. |
| 6,527,389 B2 | 3/2003 | Portney |
| 6,537,283 B2 | 3/2003 | Van Noy |
| 6,543,610 B1 | 4/2003 | Nigam |
| 6,544,286 B1 | 4/2003 | Perez |
| 6,551,307 B2 | 4/2003 | Peyman |
| 6,554,424 B1 | 4/2003 | Miller et al. |
| 6,554,425 B1 | 4/2003 | Roffman et al. |
| 6,557,998 B2 | 5/2003 | Portney |
| 6,581,993 B2 | 6/2003 | Nigam |
| 6,582,076 B1 | 6/2003 | Roffman et al. |
| 6,589,057 B1 | 7/2003 | Keenan et al. |
| 6,589,203 B1 | 7/2003 | Mitrev |
| 6,589,280 B1 * | 7/2003 | Koziol .................... 623/5.12 |
| 6,592,591 B2 | 7/2003 | Polla et al. |
| 6,596,000 B2 | 7/2003 | Chan et al. |
| 6,605,093 B1 | 8/2003 | Blake |
| 6,607,537 B1 | 8/2003 | Binder |
| 6,607,556 B1 | 8/2003 | Nigam |
| 6,623,522 B2 | 9/2003 | Nigam |
| 6,626,941 B2 | 9/2003 | Nigam |
| 6,629,979 B1 | 10/2003 | Feingold et al. |
| 6,632,244 B1 | 10/2003 | Nigam |
| 6,641,577 B2 | 11/2003 | Bille |
| 6,645,246 B1 | 11/2003 | Weinschenk, III et al. |
| 6,648,877 B1 | 11/2003 | Juhasz et al. |
| 6,657,029 B2 | 12/2003 | Vanderbilt |
| 6,666,887 B1 | 12/2003 | Callahan et al. |
| 6,673,112 B2 | 1/2004 | Nigam |

(56) References Cited

U.S. PATENT DOCUMENTS

| | | |
|---|---|---|
| 6,702,807 B2 | 3/2004 | Peyman |
| 6,709,103 B1 | 3/2004 | Roffman et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,733,526 B2 | 5/2004 | Paul et al. |
| 6,808,262 B2 | 10/2004 | Chapoy et al. |
| 6,824,178 B2 | 11/2004 | Nigam |
| 6,849,090 B2 | 2/2005 | Nigam |
| 6,855,163 B2 | 2/2005 | Peyman |
| 6,875,232 B2 | 4/2005 | Nigam |
| 6,879,402 B2 | 4/2005 | Küchel |
| 6,881,197 B1 | 4/2005 | Nigam |
| 6,893,461 B2 | 5/2005 | Nigam |
| 6,949,093 B1 | 9/2005 | Peyman |
| 6,955,432 B2 | 10/2005 | Graham |
| 7,128,351 B2 | 10/2006 | Nigam |
| 7,585,075 B2 | 9/2009 | Marmo |
| 7,699,837 B2 | 4/2010 | Cox et al. |
| 7,776,086 B2 | 8/2010 | Miller |
| 7,976,577 B2 | 7/2011 | Silvestrini |
| 7,992,906 B2 | 8/2011 | Nigam |
| 8,057,541 B2 | 11/2011 | Dishier et al. |
| 8,162,953 B2 | 4/2012 | Dishier et al. |
| 8,469,948 B2 | 6/2013 | Dishier et al. |
| 8,540,727 B2 | 9/2013 | Dishier et al. |
| 8,668,735 B2 | 3/2014 | Nigam et al. |
| 8,685,292 B2 | 4/2014 | Mandler et al. |
| 2001/0027314 A1 | 10/2001 | Peyman |
| 2001/0031959 A1 | 10/2001 | Rozakis et al. |
| 2001/0051826 A1 | 12/2001 | Bogaert et al. |
| 2002/0010510 A1 | 1/2002 | Silvestrini |
| 2002/0055753 A1 | 5/2002 | Silvestrini |
| 2002/0063068 A1 | 5/2002 | Faxe |
| 2002/0101563 A1 | 8/2002 | Miyamura et al. |
| 2002/0103538 A1 | 8/2002 | Hughes et al. |
| 2002/0138069 A1 | 9/2002 | Peyman |
| 2002/0156467 A1 | 10/2002 | Tamayo |
| 2003/0014042 A1 | 1/2003 | Juhasz et al. |
| 2003/0033010 A1 | 2/2003 | Hicks et al. |
| 2003/0069637 A1 | 4/2003 | Lynch et al. |
| 2003/0078487 A1 | 4/2003 | Jeffries et al. |
| 2003/0208190 A1* | 11/2003 | Roberts et al. .................. 606/5 |
| 2003/0220653 A1 | 11/2003 | Perez |
| 2003/0229303 A1 | 12/2003 | Haffner et al. |
| 2004/0019379 A1 | 1/2004 | Glick et al. |
| 2004/0034413 A1* | 2/2004 | Christensen ................ 623/5.11 |
| 2004/0054408 A1 | 3/2004 | Glick et al. |
| 2004/0059320 A1 | 3/2004 | Telandro et al. |
| 2004/0073303 A1 | 4/2004 | Schanzlin |
| 2005/0080484 A1 | 4/2005 | Marmo et al. |
| 2005/0080485 A1 | 4/2005 | Nigam |
| 2005/0113844 A1 | 5/2005 | Nigam |
| 2005/0119738 A1 | 6/2005 | Nigam |
| 2005/0143717 A1 | 6/2005 | Peyman |
| 2005/0178394 A1* | 8/2005 | Slade ............................ 128/898 |
| 2005/0182350 A1 | 8/2005 | Nigam |
| 2005/0182488 A1 | 8/2005 | Peyman |
| 2005/0203494 A1 | 9/2005 | Holliday |
| 2005/0222679 A1 | 10/2005 | Peyman |
| 2005/0246015 A1* | 11/2005 | Miller .......................... 623/5.11 |
| 2005/0246016 A1 | 11/2005 | Miller et al. |
| 2005/0251115 A1* | 11/2005 | Cox et al. ......................... 606/4 |
| 2005/0261752 A1 | 11/2005 | Chernyak |
| 2006/0020267 A1* | 1/2006 | Marmo .................. A61F 2/147 606/107 |
| 2006/0105309 A1 | 5/2006 | Stoll et al. |
| 2006/0116762 A1 | 6/2006 | Hong et al. |
| 2006/0134170 A1 | 6/2006 | Griffith et al. |
| 2006/0142780 A1 | 6/2006 | Pynson et al. |
| 2006/0142781 A1 | 6/2006 | Pynson et al. |
| 2006/0173539 A1 | 8/2006 | Shiuey |
| 2006/0235430 A1 | 10/2006 | Le et al. |
| 2007/0027538 A1 | 2/2007 | Aharoni et al. |
| 2007/0106318 A1 | 5/2007 | McDonald |
| 2007/0106376 A1 | 5/2007 | Roberts et al. |
| 2007/0129797 A1* | 6/2007 | Lang et al. .................. 623/5.11 |
| 2007/0182920 A1 | 8/2007 | Back et al. |
| 2007/0203577 A1* | 8/2007 | Dishler et al. ............... 623/5.11 |
| 2007/0244559 A1 | 10/2007 | Shiuey |
| 2007/0255401 A1 | 11/2007 | Lang |
| 2007/0270945 A1 | 11/2007 | Kobayashi et al. |
| 2007/0280994 A1 | 12/2007 | Cunanan |
| 2008/0039825 A1 | 2/2008 | Lai et al. |
| 2008/0228177 A1 | 9/2008 | Moritz et al. |
| 2008/0262610 A1 | 10/2008 | Lang et al. |
| 2008/0269771 A1 | 10/2008 | Fulcher |
| 2008/0281304 A1 | 11/2008 | Campbell |
| 2009/0005764 A1 | 1/2009 | Knox et al. |
| 2009/0079940 A1 | 3/2009 | Dai et al. |
| 2009/0198325 A1 | 8/2009 | Holliday et al. |
| 2009/0216217 A1 | 8/2009 | Odrich et al. |
| 2009/0326650 A1 | 12/2009 | Zickler et al. |
| 2010/0069915 A1 | 3/2010 | Shiuey |
| 2010/0241060 A1 | 9/2010 | Roizman et al. |
| 2010/0331830 A1 | 12/2010 | Bischoff et al. |
| 2010/0331831 A1 | 12/2010 | Bischoff et al. |
| 2011/0029073 A1 | 2/2011 | Liang |
| 2011/0149241 A1 | 6/2011 | Dai |
| 2011/0208300 A1 | 8/2011 | de Juan et al. |
| 2011/0218623 A1 | 9/2011 | Dishler et al. |
| 2011/0256806 A1 | 10/2011 | Monnoyeur |
| 2011/0290681 A1 | 12/2011 | Nigam |
| 2012/0203238 A1 | 8/2012 | Nigam |
| 2012/0231416 A1 | 9/2012 | Drapeau et al. |
| 2012/0238806 A1 | 9/2012 | Mangiardi et al. |
| 2012/0245592 A1 | 9/2012 | Berner et al. |
| 2012/0245683 A1 | 9/2012 | Christie et al. |
| 2013/0023892 A1 | 1/2013 | Schneider et al. |
| 2013/0060255 A1 | 3/2013 | Feingold et al. |
| 2013/0211523 A1 | 8/2013 | Southard et al. |
| 2013/0231739 A1 | 9/2013 | Dishler et al. |
| 2013/0253527 A1 | 9/2013 | Schneider et al. |
| 2013/0253529 A1 | 9/2013 | Walter et al. |
| 2013/0281993 A1 | 10/2013 | Dishler et al. |
| 2013/0317605 A1 | 11/2013 | Ide et al. |
| 2013/0324983 A1 | 12/2013 | Liang |
| 2014/0128855 A1 | 5/2014 | Wottke et al. |
| 2014/0288540 A1 | 9/2014 | Bischoff et al. |
| 2016/0184085 A1 | 6/2016 | Schneider et al. |
| 2017/0319329 A1* | 11/2017 | Muller .................... A61F 2/142 |

FOREIGN PATENT DOCUMENTS

| | | |
|---|---|---|
| EP | 0420549 A2 | 4/1991 |
| EP | 0729323 B1 | 7/1998 |
| EP | 0668061 B1 | 9/2000 |
| JP | S5973622 A | 4/1984 |
| JP | 01-195853 | 8/1989 |
| JP | 02-211119 | 8/1990 |
| JP | 5502811 | 5/1993 |
| JP | H06510687 | 12/1994 |
| JP | 08-501009 | 2/1996 |
| JP | 9-504706 | 5/1997 |
| JP | 2000506056 | 5/2000 |
| JP | 2001091910 A | 4/2001 |
| JP | 2002537895 | 11/2002 |
| JP | 03-508135 | 3/2003 |
| JP | 2006181269 A | 7/2006 |
| JP | 2007500070 | 1/2007 |
| JP | 2010507814 A | 3/2010 |
| JP | 2010220488 A | 10/2010 |
| JP | 2012523854 A | 10/2012 |
| KR | 2001-0013218 | 2/2001 |
| RU | 2294722 C2 | 3/2007 |
| WO | WO92/08423 A1 | 5/1992 |
| WO | WO93/05731 A1 | 4/1993 |
| WO | WO96/26690 A1 | 9/1996 |
| WO | WO98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |

(56) References Cited

FOREIGN PATENT DOCUMENTS

| | | |
|---|---|---|
| WO | WO 03/041616 A1 | 5/2003 |
| WO | WO 03/061518 A2 | 7/2003 |
| WO | WO 03/101341 A2 | 12/2003 |
| WO | WO 2005/020792 A2 | 3/2005 |
| WO | WO2005/082265 A1 | 9/2005 |
| WO | WO 2005/107648 A2 | 11/2005 |
| WO | WO 2006/029316 A1 | 4/2006 |
| WO | WO 2006/060363 A2 | 6/2006 |
| WO | WO2006/083708 A2 | 8/2006 |
| WO | WO 2007/101016 A2 | 9/2007 |
| WO | WO 2007/132332 A2 | 11/2007 |
| WO | WO2010/084595 A1 | 7/2010 |
| WO | WO2011/069907 A1 | 6/2011 |

OTHER PUBLICATIONS

Patel et al.; Refractive index of human corneal epithelium and stroma; J. Refract. Surg.; 11(2); Abstract; Mar. 1995 (pubmed Abstract only).

Esguerra et al.; U.S. Appl. No. 14/463,355 entitled "Corneal implant storage, packaging, and delivery devices," filed Aug. 19, 2014.

Alio, J. J., et al., "Intracorneal Inlay Complicated by Intrastomal Epithelial Opacification," Arch Ophthalmol, Oct. 2004; vol. 122; 6 pages.

Cheng, et al.; "Predicting subjective judgment of best focus with objective image quality metrics"; Journal of Vision; Apr. 23, 2004; vol. 4(4); pp. 310-321.

Churms, P.W., "The Theory and Computation of Optical Modifications to the Cornea in Refractive Keratoplasty," American Journal of Optometry & Physiological Optics, 56:2, pp. 67-74, Feb. 1979.

Huang et al.; Mathematical Model of Corneal Surface Smoothing After Laser Refractive Surgery; American Journal of Ophthalmology; Mar. 2003; pp. 267-278.

Lang, A.J. et al., "First order design of intracorneal inlays: dependence on keratometric flap and corneal properties," ARVO Abstracts 2006, poster No. 3591, May 3, 2006.

Liou, H. L. et al., "Anatomically accurate, finite model eye for optical modeling", Journal of the Optical Society of America, vol. 14, No. 8, Aug. 1997.

Marsack,et al.; "Metrics of optical quality derived from wave aberrations predict visual performance"; Journal of Vision; Apr. 23, 2004; vol. 4(4); pp. 322-328.

Navarro et al.; Accommodation-dependent model of the human eye with aspherics; J. Opt. Soc Am. A; vol. 2; No. 8; Aug. 1985; pp. 1273-1281.

Petroll et al.; Confocal assessment of the cornal response to intracorneal lens insertion and laser in situ keratomileusis with flap creation using IntraLase; J Cataract Refract Surg; vol. 32; pp. 1119-1128; Jul. 2006.

Reinstein et al.; Change in epithelial thickness profile 24 hours and longitudinally for 1 year after myopic LASIK: three-dimensional display with Artemis very high-frequency digital ultrasound; J Refract Surg. Mar. 2012; 28(3):195-201.

Reinstein et al.; Epithelial thickness up to 26 years after radial keratotomy: three-dimensional display with Artemis very high-frequency digital ultrasound; J Refract Surg. Aug. 2011; 27(8):618-624.

Reinstein et al.; Epithelial, stromal, and total corneal thickness in keratoconus: three-dimensional display with artemis very-high frequency digital ultrasound; J Refract Surg. Apr. 2010; 26(4):259-71.

Reinstein et al.; Epithelial thickness after hyperopic LASIK: three-dimensional display with Artemis very high-frequency digital ultrasound; J Refract Surg. Aug. 2010;26(8):555-64.

Reinstein et al.; Corneal epithelial thickness profile in the diagnosis of keratoconus; J Refract Surg. Jul. 2009; 25(7):604-10.

Reinstein et al.; Stability of LASIK in topographically suspect keratoconus confirmed non-keratoconic by Artemis VHF digital ultrasound epithelial thickness mapping: 1-year follow-up; J Refract Surg. Jul. 2009; 25(7):569-77.

Reinstein et al.; Epithelial, stromal, and corneal pachymetry changes during orthokeratology; Optom Vis Sci. Aug. 2009; 86(8):E1006-14.

Reinstein et al.; Epithelial thickness profile changes induced by myopic LASIK as measured by Artemis very high-frequency digital ultrasound; J Refract Surg. May 2009; 25(5):444-50 (Author manusript).

Reinstein et al.; Epithelial thickness in the normal cornea: three-dimensional display with Artemis very high-frequency digital ultrasound; J Refract Surg. Jun. 2008; 24(6):571-81 (Author manusript).

Reinstein et al.; Epithelial and stromal changes induced by intacs examined by three-dimensional very high-frequency digital ultrasound; J Refract Surg. May-Jun. 2001; 17(3):310-8.

Reinstein et al.; Epithelial and corneal thickness measurements by high-frequency ultrasound digital signal processing; Ophthalmology. Jan. 1994; 101(1):140-6.

Reinstein et al.; High-frequency ultrasound measurement of the thickness of the corneal epithelium; Refract Corneal Surg. Sep.-Oct. 1993;9(5):385-7.

Serrao et al.; Corneal epithelial healing after photorefractive keratectomy: analytical study; J. Cataract Refract Surg; vol. 31; pp. 930-937; May 2005.

Thoft et al.; The X, Y, Z Hypothesis of Corneal Epithelial Maintenance; Investigative Ophthalmology & Visual Science; vol. 24; pp. 1442-1443; Oct. 1983.

Watsky, M.A. et al., "Predicting Refractive Alterations with Hydrogel Keratophakia," Investigative Opthalmology & Visual Science, vol. 26, pp. 240-243, Feb. 1985.

Nigam et al.; U.S. Appl. No. 14/160,438 entitled "Coreal Implant Applicators," filed Jan. 21, 2014.

Sharma et al.; U.S. Appl. No. 14/211,714 entitled "Pre-treatment haze reduction for corneal inlays," filed Mar. 14, 2014.

Plambeck et al.; U.S. Appl. No. 14/352,628 entitled "Corneal implant storage and delivery devices," filed Apr. 17, 2014.

Holliday et al.; U.S. Appl. No. 14/547,931 entitled "Corneal inlay design and methods of correcting vision," filed Nov. 19, 2014.

Collins et al.; U.S. Appl. No. 14/575,833 entitled "Integrated part fixturing for lathing processes," filed Dec. 18, 2014.

Sharma; U.S. Appl. No. 14/427,510 entitled "Corneal implant edges and methods of use," filed Mar. 11, 2015.

Holliday et al.; U.S. Appl. No. 14/656,621 entitled "Methods of correcting vision," filed Mar. 12, 2015.

Esguerra et al.; U.S. Appl. No. 14/688,226 entitled "Corneal implant delivery devices and methods of use," filed Apr. 16, 2015.

Dymax; UV curable optical assembly; 2 pages; retrieved Mar. 4, 2015 from the internet (http:www.dymax.com/index.php/adhesives/optical).

Jankov et al.; Laser intrastromal keratoplasty—case report; J. Refract. Surg.; 20(1); pp. 79-84; Jan.-Feb. 2004.

Winn et al.; Factors affecting light-adapted pupil size in normal human subjects; Investigative Ophthalmology and Visual Science; 35(3); pp. 1132-1137; Mar. 1994.

Walker et al.; Clinical Methods: The history, physical, and laboratory examinations; 3rd Edition; Chapter 58; Butterworth Publishers; Jul. 1990; 8 pages; retrieved from the internet (http://www.ncbi.nlm.nih.gov/books/NBK381).

Plambeck et al.; U.S. Appl. No. 15/163,610 entitled "Corneal implant storage and delivery devices," filed May 24, 2016.

Dishler et al.; U.S. Appl. No. 15/219,130 entitled "Small diameter corneal inlays," filed Jul. 25, 2016.

Holliday; U.S. Appl. No. 15/313,297 entitled "Corneal implants and methods of manufacturing," filed Nov. 22, 2016.

Holliday et al.; U.S. Appl. No. 15/403,078 entitled "Methods of correcting vision," filed Jan. 10, 2017.

Schneider et al.; U.S. Appl. No. 15/413,269 entitled "Corneal implant inserters and methods of use," filed Jan. 23, 2017.

Le et al.; U.S. Appl. No. 15/508,499 entitled "Training cornea for refractive surgery training," filed Mar. 3, 2017.

Daxer et al.; Collagen fibrils in the human corneal stroma: Structure and aging; Ivest Opthalmol & Vis Sci.; 39(3); pp. 644-648; Mar. 1998.

\* cited by examiner

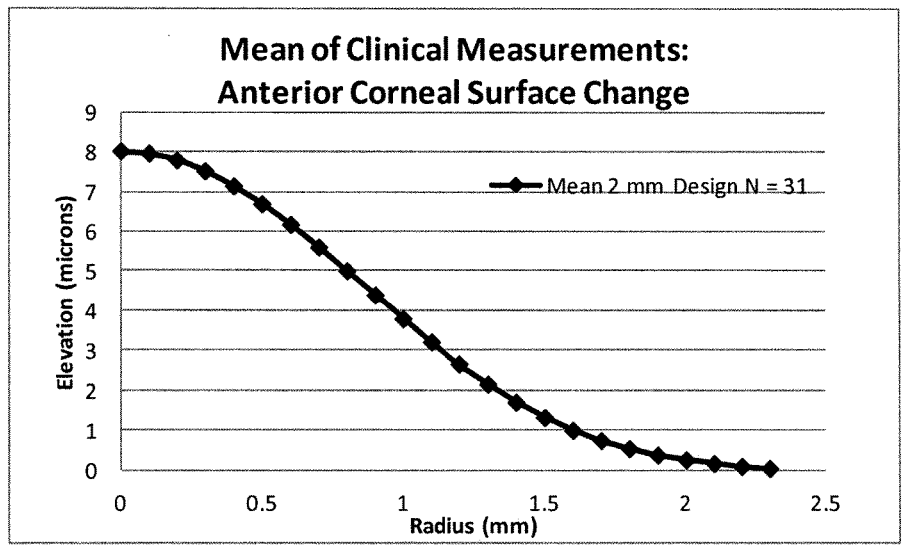
Figure 1: Mean change of the anterior corneal surface from clinical data, for each design.
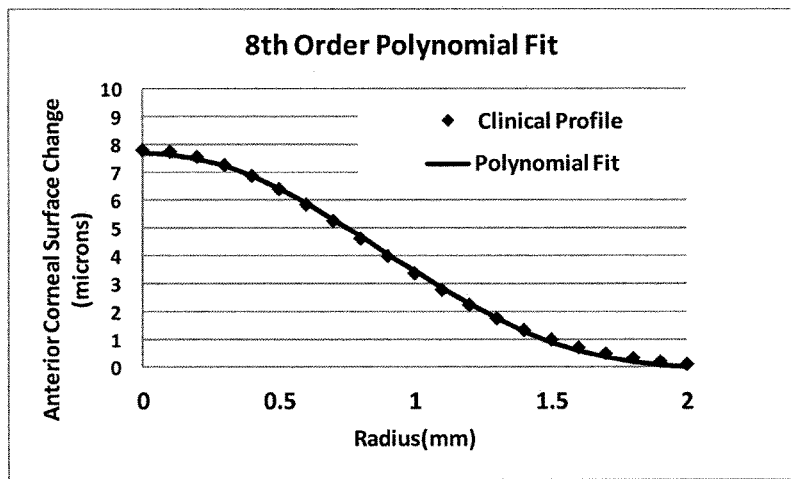
Figure 2: Demonstration that an 8$^{th}$ order polynomial accurately fits the measured anterior corneal surface change.

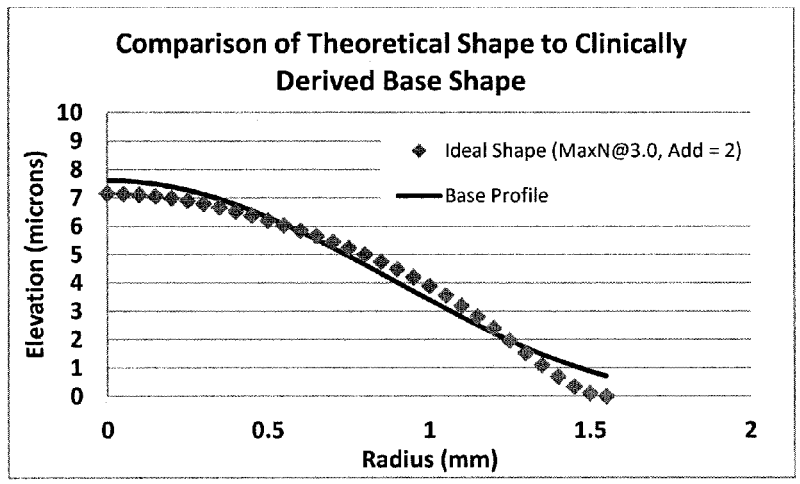
Figure 3
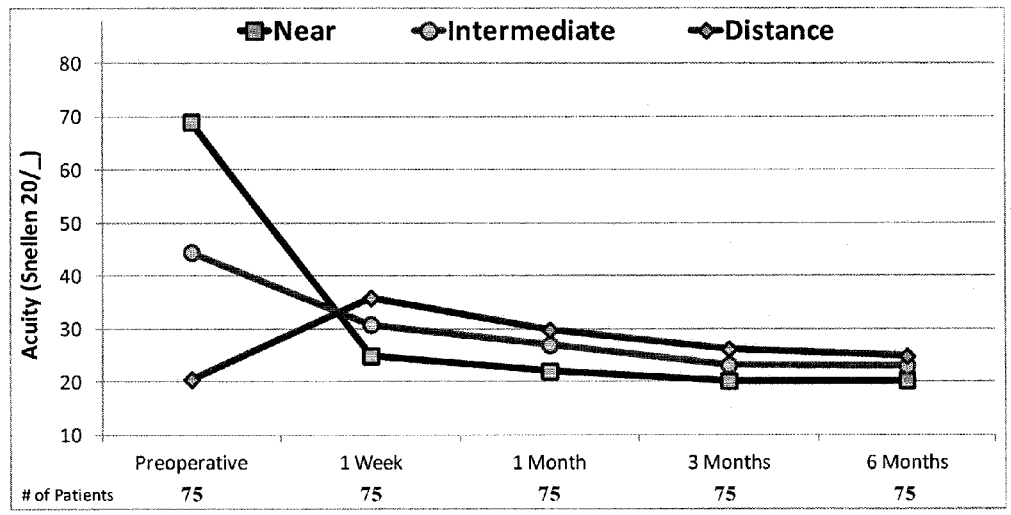
Figure 4: Clinical performance of subjects implanted with the inlay design.

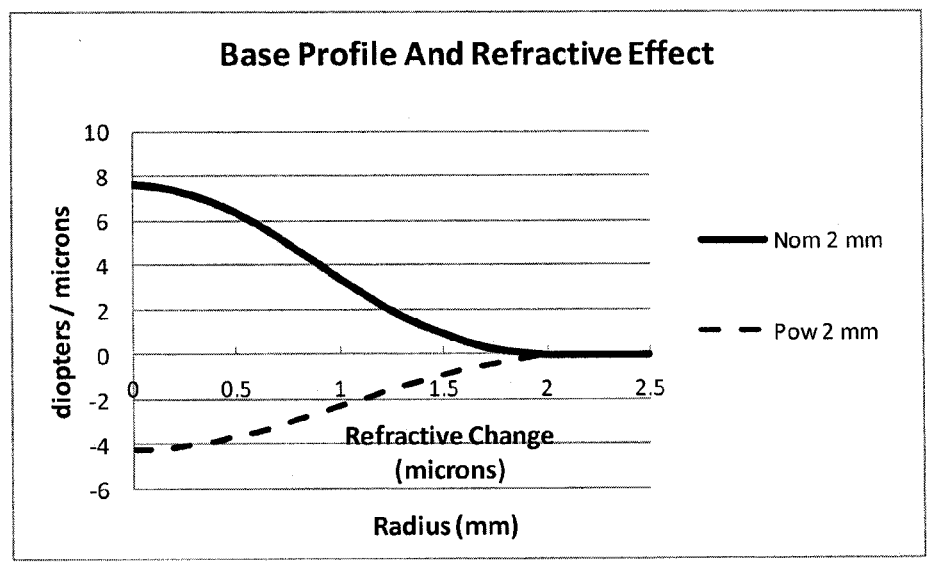
Figure 5: Elevation and refractive change provided by the base design.

ANTERIOR CORNEAL SHAPES AND METHODS OF PROVIDING THE SHAPES

CROSS REFERENCE TO RELATED APPLICATIONS

This application claims priority to U.S. Prov. App. No. 61/799,847, filed Mar. 15, 2013, which is incorporated by reference herein.

This application is also a continuation-in-part of U.S. application Ser. No. 12/877,799, filed Sep. 8, 2010, now abandoned, which is incorporated by reference herein.

This application is also a continuation-in-part of pending U.S. application Ser. No. 12/418,325, filed Apr. 3, 2009, now U.S. Pat. No. 8,900,296. U.S. application Ser. No. 12/418, 325 also claims priority to U.S. Prov. App. No. 61/042,659, filed Apr. 4, 2008 and U.S. Prov. App. No. 61/155,433, filed Feb. 25, 2009. All of the aforementioned applications are incorporated by reference herein.

This application is related to and incorporates herein by reference the following U.S. patent applications: 60/776, 548, filed Feb. 24, 2006; Ser. No. 11/554,544, filed Oct. 30, 2006; 61/042,659, filed Apr. 4, 2008; 61/155,433, filed Feb. 25, 2009; Ser. No. 11/738,349, filed Apr. 20, 2007; and Ser. No. 12/418,325, filed Apr. 3, 2009.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Corneal procedures can be performed that reshape the anterior surface of the cornea, and therefore change the refraction of the cornea. While the initial procedure can cause an immediate change to the shape of the anterior surface of the cornea, the cornea, after some period of time following the procedure, may respond biologically to the procedure. The biological response can modify the shape relative to the immediate post-procedure shape. The final shape of the anterior surface of the cornea therefore depends on both the change induced by the procedure as well as the biological response of the cornea. When determining how to achieve a particular refraction correction for a patient, it is therefore not only important to understand the immediate effect the procedure will have on the anterior surface of the cornea, but also any biological response the cornea may have to the procedure.

One method of changing the curvature of the anterior surface of the lens is by implanting a corneal inlay within the cornea. Some inlays do not have intrinsic power because the index of refraction of the inlay material is the same, or substantially the same, as the cornea. Thus, there is no significant refraction of light at the inlay/cornea interface. For these inlays, the entire refractive effect on the eye is achieved due to the shape change to the anterior surface of the cornea. Reshaping the anterior corneal surface is very effective in altering the optical properties of the human eye because the index of refraction difference is large at the air/anterior corneal surface boundary, i.e., the difference is 1.376−1. Very strong "bending" of light occurs at the anterior corneal surface. However, the biological response of the cornea to the inlay must also be taken into account.

For some types of inlays it was originally thought that the profile of the change to the cornea was the same as the inlay profile. For example, it was thought that the anterior surface of the inlay would translate almost or substantially exactly and cause the cornea anterior surface to assume the same shape. For corneal inlays described in U.S. patent applications: 60/776,548, filed Feb. 24, 2006; Ser. No. 11/554,544, filed Oct. 30, 2006; 61/042,659, filed Apr. 4, 2008; 61/155, 433, filed Feb. 25, 2009; Ser. No. 11/738,349, filed Apr. 20, 2007; and Ser. No. 12/418,325, filed Apr. 3, 2009, which are incorporated by reference herein, however, it has empirically been shown by the Applicants that the final anterior corneal shape is not, in fact, the same as the shape of the corneal inlay. For example, the cornea's biological response to an inlay's implantation was clinically observed in U.S. Pat. No. 8,057,541, filed Oct. 30, 2006 (the disclosure of which is incorporated herein by reference), where it was observed that the central anterior surface elevation change was less than the center thickness of the inlay. The cornea's biological response to the inlays was also discussed in U.S. Pub. No. 2008/0262610, filed Apr. 20, 2007, and in U.S. Pub. No. 2009/0198325, filed Apr. 3, 2009, the disclosures of which are incorporated by reference herein. Because the final shape of the anterior surface of the cornea will not simply be the same as the shape of the inlay, the question remains how to achieve the final anterior corneal surface shape.

SUMMARY OF THE DISCLOSURE

One aspect of the disclosure is a method of performing a vision correction procedure, comprising calculating an $8^{th}$ order polynomial base shape for a central region of the patient's anterior corneal surface, wherein the base shape provides for near and distance vision within the pupil; selecting a corneal inlay for implantation within the cornea that will change the shape of the anterior cornea surface to the $8^{th}$ order polynomial.

In some embodiments the method further comprises scaling the $8^{th}$ order polynomial base shape to provide a desired amount of near and distance visual acuity for the patient, and wherein the selecting step comprises selecting an inlay for implantation that will change the shape of the anterior corneal surface to the scaled $8^{th}$ order polynomial. Scaling can comprise changing the central height of the $8^{th}$ order polynomial base shape. Scaling can comprise changing the radial dimension of the $8^{th}$ order polynomial base shape. Scaling the $8^{th}$ order base shape can enhance near visual acuity and reduce distance visual acuity. Scaling the $8^{th}$ order base shape can enhance distance visual acuity and reduce near visual acuity.

In some embodiments selecting the inlay for implantation comprises selecting an inlay with an anterior surface with a shape that is not an $8^{th}$ order polynomial.

BRIEF DESCRIPTION OF FIGURES

FIG. 1 plots the mean change to the anterior corneal surface (height profile) for a 2.0 mm diameter inlay design, using the clinically measured height profiles for 31 subjects.

FIG. 2 demonstrates that height profile (P) for the 2.0 mm design is accurately given by the coefficients ($a_n$) of a symmetric $8^{th}$ order polynomial.

FIG. 3 provides a comparison between the theoretical design targeting an add power of 2 Diopters and a maximum near image quality at 3 mm pupil (see Table 1), and the clinically derived "base" shape.

FIG. 4 presents the distance, intermediate and near visual acuity for 75 subjects in a clinical study.

FIG. 5 shows the base profile that is the average response to the 2 mm inlay, using the 8th order polynomial to fit.

DETAILED DESCRIPTION

Figure 6:
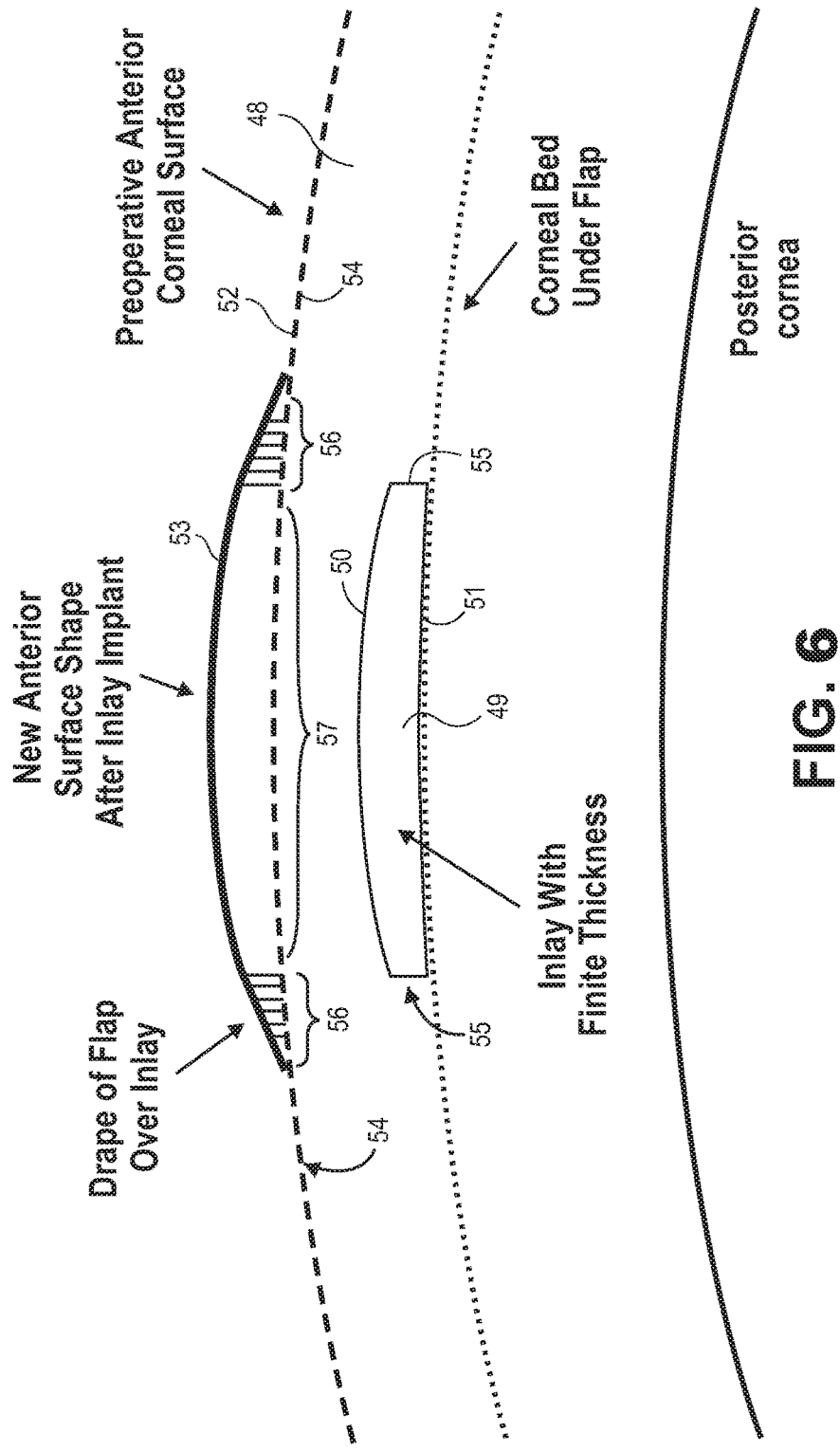
FIG. 6 is a cross-sectional view of a cornea showing an inlay implanted in the cornea and a change in the anterior corneal surface induced by the inlay, including a drape region according to an embodiment of the invention.

The disclosure herein provides a method of determining a desired shape for the anterior surface of the cornea. The response of the corneal tissue to the inlay's shape and volume is first determined, especially of the stroma and epithelium anterior to the inlay. This response is reduced to a functional relationship predicting the change to the anterior corneal surface for a given inlay design. By other techniques, such as optical design analysis or empirical analysis of clinical data, the desired optical effect is then determined, and the targeted anterior corneal surface required is then calculated. Using the functional biological relationship from the previous step, the required inlay design (shape and volume) is then calculated.

The disclosure herein discloses the nominal shape of an anterior corneal surface that can be produced by implanting a corneal inlay in the corneal stroma using a LASIK flap or otherwise, and that provides good distance, intermediate and near vision. Nominal shapes are provided for an exemplary 2.0 mm diameter inlay design.

The method of determining the surface shape of the anterior surface of the cornea herein includes using clinical measurement of the anterior corneal surface change after a 2.0 mm diameter inlay was implanted to show that the anterior corneal surface change can be fit to an $8^{th}$ order symmetric polynomial. Using a surface description constrained to an $8^{th}$ order symmetric polynomial, a range of shapes optimal for near and distance vision is then derived by theoretical ray trace methods. This aspect is described in detail in US Pub. No. 2009/0198325, incorporated herein by reference. The average of the anterior corneal surface shape change for subjects with the 2 mm diameter design establishes the ideal corneal shape because the clinical data demonstrates good distance, intermediate, and near visual acuity in the treated eye. This inlay design also provides a shape that is within the range of the theoretically ideal shapes from ray-trace analysis. The method also illustrates that there is a nominal basic biomechanical "shape," from which each individual subject's anterior corneal surface shape can be calculated, by a scaling of the central height change and the diameter of the anterior corneal surface effect.

Background and Methods. The disclosure describes the determination of a desired anterior corneal shape. The anterior corneal shape for a given corneal inlay subject is derived from wavefront measurements recorded with the Tracey aberrometer. The wavefront is a measure of the optical properties of any optical system. If the only change to the human eye is the presence of the inlay, then by subtracting the postoperative wavefront from the preoperative wavefront, one derives the change due to only the inlay. The wavefront (WF) difference map provides a 3D profile of the anterior corneal surface change. The 3D height profile is calculated from the WF difference map by dividing by the cornea-air index of refraction difference (1.376−1).

To calculate the mean radial anterior corneal surface height change profile ("height profile"), for a given subject, we average the three dimensional ("3D") height profile in 32 radial meridians, around the full 3D profile, centered on the peak of the 3D height profile.

The data presented in this analysis was derived from clinical studies. FIGS. 2 and 3 show the mean response for implantation of the 2.0 mm diameter inlay, while FIG. 3 also shows the ideal curve from Table 1. Table 1 provides ideal anterior corneal surface changes for three spectacle ADD powers (1.5 diopters, 2.0 diopters, and 2.5 diopters) and for three pupil sizes (small, nominal and large) when using near vision, derived theoretically by ray-trace analysis, which is described below.

Parameterization of the Anterior Corneal Surface Change. Because the inlay is circularly symmetric, the change to the anterior corneal surface is substantially symmetric. It is of note that while the term "symmetric" is used herein, it is understood that this term or derivatives of it include surfaces or changes that are not perfectly symmetric, but are substantially symmetric. For example, corneal flaps are not perfectly symmetrical since they have a hinge, and thus the final shape change may not be perfectly symmetrical. These shape changes are still considered symmetric as that term is used herein. The functional representation of the anterior corneal surface is thus generally an even function of the radius. FIG. 1 plots the mean change to the anterior corneal surface (height profile) for a 2.0 mm diameter inlay design, using the clinically measured height profiles for 31 subjects. FIG. 2 demonstrates that height profile (P) for the 2.0 mm design is accurately given by the coefficients ($a_n$) of a symmetric $8^{th}$ order polynomial. The parameterized anterior corneal shape formula is:

$$P(r)=[a0+a2(r)^2+a4(r)^4+a6(r)^6+a8(r)^8]$$

The first step in correcting the vision of a subject by altering the cornea is generally determining the desired post-operative shape of the anterior corneal surface which will provide the desired refractive power change (i.e., determining the shape change for the anterior surface of the cornea). The shape of the desired anterior surface may be the result of a biomechanical response as well as epithelial remodeling as a result of the vision correction procedure. Corneal epithelial remodeling will be described in more detail below. Based on a biomechanical response and an epithelial response, the vision correction procedure is performed (e.g., implanting an inlay) to induce the desired anterior surface change. This disclosure includes an exemplary method of determining a desired anterior corneal shape to provide for corrective vision. One particular embodiment in which the method includes implanting an inlay within the cornea to provide for a zone in the center of the cornea that provides near vision and a zone in the periphery that provides distance vision will be described. In some embodiments a central zone on the anterior corneal surface with a sharp transition is preferred (i.e., substantially without an outer effect zone). A sharp transition maximizes both the near and distance power efficiencies. In practice, the effects of epithelial remodeling typically prevent "sharp" transitions. Empirically, the anterior surface change induced by the inlay can be given by a symmetric polynomial of at least eighth order:

$$\text{Elev}(r)=a0+\alpha a2{\times}r^2+a4{\times}r^4+a6{\times}r^6+a8{\times}r^8$$

Where "Elev" is the change in anterior corneal surface elevation due to the inlay, a0, a2, a4, a6 and a8 are the coefficients governing the shape And "r" is the radial extent location from the center of the anterior surface change.

The elevation change discussed herein is azimuthally symmetric in plane perpendicular to the axis of the cornea. In other embodiments, however, orthogonal asymmetries may be included with more complex inlay designs, attempting to correct for corneal astigmatism, pre-existing in the subject's eye. Physically, there are useful restrictions on the form of the elevation expression. At r=0, the elevation change is maximal and is central height "hctr". From the symmetry, at r=0, the first derivative of elevation expression must be zero. The extent of the inlay-induced change is limited to a maximal radius ($r_z$), where Elev($r_z$)=0. And because the elevation smoothly transitions to the original cornea at $r_z$, the first derivative is normally also zero; i.e., dElev($r_z$)/dr=0.

With these restrictions, the elevation change can be characterized by four independent parameters: hctr, $r_z$, a6 and a8. And the remaining coefficients are given by:

$$a0=hctr$$

$$a2=2*alpha/rz^2-beta/2/rz$$

$$a4=beta/2/rz^3-alpha/rz^4$$

Where:

$$alpha=-hctr-a6*rz^6-a8*rz^8$$

$$beta=-6*a6*rz^5-8*a8*rz^7$$

Thus, the ideal anterior corneal elevation change can be expressed by four independent parameters: hctr, $r_z$, a6 and a8.

Table 1 provides ideal anterior corneal surface changes for three spectacle ADD powers (1.5 diopters, 2.0 diopters, and 2.5 diopters) and for three pupil sizes (small, nominal and large) when using near vision, derived theoretically by ray-trace analysis, which is described below.

Performing the optical ray-trace optimization to derive the optimal anterior corneal elevation change (Elev) requires a model eye which mimics the key optical functions of the human eye. The finite eye model by Navarro (Accommodation dependent model of the human eye with aspherics, R. Navarro. Et al, JOSA Vol 2 No 8 1985 p. 1273-1281) provides one such model. For these design purposes, the Navarro model provides anatomically correct values for the corneal physical and optical properties and provides total eye properties such as normal values for the total eye spherical aberrations, chromatic aberration and Stiles-Crawford effect. Other model eyes can be also used.

To include the anterior corneal elevation change (Elev) in the Navarro eye model, the Elev surface is added to the anterior surface of the Navarro eye model. Calculations of the image quality created by the anterior surface change to the eye model are accomplished using any of many commercial ray-trace software packages. For the examples provided, the Zemax-EE Optical Design Program (2008) from the Zemax Development Corporation was used.

The objective of the ray-trace optimization is to find the elevation surface parameters (hctr, $r_z$, a6 and a8) that maximize the optical performance for a given set of assumptions. There are many optical metrics of image quality used in optical design. Of these, the Modulation Transfer Function (MTF) is particularly useful for optical designs, using any combination of optical surfaces of any shape. The MTF is the efficiency of transferring the contrast of the original object to the contrast of the image of the object on the human retina. The MTF efficiency (modulation) is plotted as a function of the spatial frequency information in the image of the object. The spatial frequency can be thought of as one divided by the size of features in the image. Thus, large spatial frequencies represent very fine features in the object, and low spatial frequencies represent very large features in the object. The image quality is maximized when the MTF values at targeted spatial frequencies have their highest values.

The assumptions are derived from the inlay's design requirement to provide a good distance image from light rays passing mainly through the peripheral region between the pupil diameter and the inlay's effect zone ($r_z$), and a good near image for light rays passing through the central effect zone. Thus, the ray-trace program is set with at least two configurations. In the first, the object for the eye model is set to infinity (e.g., looking at a distant object). In the second configuration, the object is set at a near distance. The typical distance of near work and ophthalmic prescription is 40 cm, which corresponds to a spectacle power requirement of 2.5 diopters.

For each configuration, the model eye's pupil size must be set. Of the many choices, two are the most logical. In the first, the pupil size is set the same for both configurations and the goal of the optimization is to find the elevation parameters which give equal distance and near image quality. The second choice is to set separate pupil sizes for the distance and near configurations. The near configuration pupil size is set to subject's pupil size in a well illuminated setting i.e., the peripheral distance zone is effectively zero. This condition provides the maximal near distance capability. The distance configuration pupil size is set to the subject's night-time or dim-light pupil size, where distance vision is maximized. For the examples provided herein, the latter method was used, using different pupil sizes for the distance and near configurations. Note that regardless of the method chosen, the same range of ideal elevation profiles (e.g., Table 1) will be found.

The human pupil size varies for a given set of illumination conditions, with two important trends. As an individual ages, the nighttime pupil size decreases. Additionally, when looking at a near object, the pupil diameter reduces by about 0.5 mm. Based on literature and clinical experience, the near configuration pupil in bright lighting is considered "small" if approximately 2.5 mm in diameter, "nominal" if approximately 3.0 mm, and "large" if approximately 3.5 mm in diameter. For the distance configuration, the nighttime pupil sizes vary greatly, and any loss of distance vision is compensated for by the fellow eye. Thus, one nighttime pupil size is sufficient for design purposes and a diameter of 5.0 mm is suggested by the literature/clinical experience.

The optimization tools of the ray-trace software program are now utilized. The elevation parameters (hctr, $r_z$, a6 and a8) are varied until the MTF of the near configuration is maximized while simultaneously maximizing the MTF of the distance configuration. The ideal design is clearly a function of the assumed pupil sizes. In practice, subject may be screened preoperatively, allowing the surgeon to select the inlay design most appropriate for the subject's pupil size range and desired visual outcome.

Clinically Derived Optimal Anterior Corneal Surface Profile. Though the theoretical analysis provides a range of theoretical ideal optical designs (Table 1), for the assumptions noted, the analysis does not guarantee that the precise predicted anterior corneal shapes are realizable. For example, some $8^{th}$ order polynomial shapes with a certain degree of steepness are not realizable. Biomechanics limit the combinations of coefficients that can be obtained. FIG. 3 provides a comparison between the theoretical design targeting an add power of 2 Diopters and a maximum near image quality at 3 mm pupil (see Table 1), and the clinically derived "base" shape. The base profile shown in FIG. 3 was derived from the implantation of 2.0 mm diameter inlays whose central thickness varied between about 32-36 microns. The figure demonstrates agreement between the two shapes, illustrating that the theoretical shape and the base profile are substantially the same. This comparison illustrates that the selection and use of the 2.0 mm diameter design provides a base shape that falls within the theoretically ideal shape. This type of comparison, which is made only after empirical data is obtained, allows a determination to be made about a preferred inlay design that will achieve the desired base shape, or scaled version thereof. Additionally, the 2.0 mm diameter design base profile provides an hctr value in the same 7-8 micron range of the ideal shape.

FIG. 1 provides the mean height profile for 31 subjects with the 2 mm design. And, again, the 2 mm clinical height profiles are within the theoretical ideal range in Table 1.

As shown in FIG. 3 the "hctr" value (the elevation change at its central height) is close to the center of the range of 5-10 microns, which covers the ideal hctr value for most ideal anterior corneal shapes, as shown in Table 1. Thus this range provides for good near vision while maintaining good distance vision for a variety of different preferred refractive adds and pupil size combinations. As there is some level of biological variation from patient to patient, being close to the center of this region, on average, is likely to be effective for a broad range of patients. The base profile shown in FIG. 3 was derived from the implantation of inlays whose central thickness varied between about 32-36 microns. For a 7 micron hctr value and a 35 micron inlay central thickness, for example, the inlay central thickness is five times the hctr. Understanding the relationship between a selected inlay thickness and the actual hctr value helps predict how the cornea will actually respond to the presence of the inlay. For example, if the desired hctr value is between about 5 and about 10 microns, the inlay to be implanted could be selected to have a central thickness that is about 5 times the desired hctr value but may be varied if other values of hctr are preferred.

The disclosure herein generally provides for methods of treating presbyopia by creating a central near vision zone while maintaining a peripheral distance vision zone (both within the pupil). There is a tradeoff between near and distance visual acuity. More near visual acuity generally results in less distance visual acuity, and likewise more distance visual acuity results in less near visual acuity. Depending on the patient and the specific type of vision correction, there may be instances where it is desirable to achieve more near vision acuity while sacrificing some distance vision. Similarly, in some instances it may be desirable to retain as much distance vision as possible, and thus limit the amount of reshaping that occurs to the anterior corneal surface. While the disclosure herein focuses on vision correction procedures that provide for both good near vision and good distance vision for a variety of different preferred refractive adds and pupil size combinations, it may be desirable to perform vision correction procedures that provide for either more near, and thus less distance, or more distance, and thus less near. Thus the disclosure herein describes methods of tailoring a vision correction to a particular patient, or to a group of patients, as opposed to using a single inlay for all vision correction procedures to treat presbyopia. By way of example, inlays with a diameter larger than 2.0 mm, such as between about 2.75 mm to about 3.25 mm (e.g., 2.8 mm, 2.9 mm, 3.0 mm, 3.1 mm, 3.2 mm), can be implanted in the cornea to provide more near visual acuity and less distance visual acuity than an inlay with a diameter of about 2.0 mm. The reason is that, generally, as the diameter of the inlay that is implanted increases in size, more of the anterior corneal surface changes shape, and thus more near visual acuity is provided while reducing the amount of distance visual acuity. Similarly, if more distance vision is desired, the inlay for implantation can be designed to be thinner in the central region. In general a thinner central height will act to reduce the shape change, thus reducing the near vision and maintaining more distance vision. The inlay can thus be selected based on the desired vision correction.

In some embodiments there could be a plurality of different inlays to be chosen from based on the individual needs of the patient. Alternatively, a patient-specific inlay could be designed and implanted.

For example, hctr values in the 2-5 micron range (i.e., less than the exemplary 5-10 micron range above) will, however, also provide vision correction. In these methods some near vision will still be provided to the patient, with less compromise to the distance vision than hctr values in the 5-10 micron range.

This 2 mm design response demonstrates good visual acuity. FIG. 4 presents the distance, intermediate and near visual acuity for 75 subjects in a clinical study. The distance, intermediate and near visual acuities achieve about 20/25 or better at 6 months.

Mean Biomechanical Corneal Response For Good Clinical Outcomes. Based on the observations above, it is apparent that a "base" anterior corneal height profile exists, representing the fundamental response of the cornea's stroma and epithelium to the inlay shape and volume. And the anterior height profile for each subject is a scaling in height and effect radius, from the base anterior corneal height profile. The individual subject response is a modification of the basic biomechanical response, due to more subtle changes between subjects. These changes include differences in the eye lid forces, differences in epithelial layer thicknesses, and possible differences in the structure of the stromal tissue, above the inlay.

A unique "base" profile exists with a set of coefficients $(a_n)$, and individual subject profiles vary depending on two parameters: a scaling in the magnitude of the profile $(\delta_i)$ and a scaling in the radial direction $(\alpha_i)$. The general form of the individual subject fit becomes:

$$P_i(r)=\delta_i[a0+a2(\alpha_i r)^2+a4(\alpha_i r)^4+a6(\alpha_i r)^6+a8(\alpha_i r)^8]$$

where each subject is "i", and a0 to a8 are the coefficients of the basic shape. Each subject's anterior corneal shape is given by a specific combination of $\delta_i$ and $\alpha_i$. A statistical recursive fit analysis yielded the parameters for the base shape and the individual subject scaling parameters for the two inlay designs.

Table 2 lists the individual subject scaling parameters ($\delta_i$ and $\alpha_i$), and the base profile fit parameters ($a_n$) for the 2.0 mm diameter inlay design. The root mean square difference between the individual subject fit and the original clinical data, as a percentage of the base shape's central height ($a_0$) is also provided. The majority of values are less than about 3%.

The base anterior height profile is shown in FIG. 3 by the black solid line.

In FIG. 5, the base profile is the average response to the 2 mm inlay, using the 8th order polynomial to fit. This is shown with the solid line. The dashed line is the refractive power that is calculated from the Base Profile.

While the disclosure herein describes the methods of determining and creating desired shapes by implanting an inlay within the cornea, other techniques can be used to create these shapes. For example, a LASIK procedure can be carried out to achieve the shapes herein. An example would be in the case of presby LASIK, a surgical technique for presbyopic visual correction using Excimer LASER ablation. Alternatively, the shapes can be achieved using INTRACOR, which uses a femtosecond laser to treat presbyopia. Other corneal reshaping methods include corneal thermoplasty (CT) and alteration of the corneal shape by cross-linking.

As set forth herein, it is useful to identify a nominal and/or range of anterior surface changes that provide good distance, intermediate and near vision for corneal inlay designs that are described as modifying the anterior corneal surface shape as described in U.S. patent applications: 60/776,548, filed Feb. 24, 2006; Ser. No. 11/554,544, filed Oct. 30, 2006; 61/042,659, filed Apr. 4, 2008; 61/155,433, filed Feb. 25, 2009; Ser. No. 11/738,349, filed Apr. 20, 2007; and Ser. No. 12/418,325, filed Apr. 3, 2009. If the design is to be changed, knowledge of the desired anterior corneal surface and the range of anterior surfaces allows prediction of acceptable new inlay designs. The methods herein of determining a desired shape of an anterior corneal surface can be used for other approaches, and are not limited to determining shapes due to the implantation of an inlay. For example, the methods can be used in determining shapes based on LASIK procedures. Additionally, the methods herein can be used for procedures that change the shape of the cornea following the removal of a lens-shaped portion of stromal tissue that may be cut by, for instance, a femtosecond laser. The shape of the lens can be modified to create a final corneal shape as described herein.

In FIG. 6, the portion of the anterior corneal surface directly above the inlay is altered by the physical shape of the inlay 49. Because of the finite edge thickness 55 of the inlay 49, the anterior corneal surface does not immediately return to its pre-implant shape for a diameter larger than the physical inlay 49. Eventually, the anterior corneal surface returns to the pre-implant corneal surface 52. Therefore, the draping effect produces a drape region 56 that extends the shape change of the anterior corneal surface induced by the inlay 49.

In some embodiments the inlay has a diameter between about 1 mm and about 3 mm, and in some particular embodiments the inlay is about 2 mm in diameter. In some embodiments the inlay central thickness (from anterior to posterior surfaces) is about 20 microns to about 40 microns, while in some particular embodiments the inlay central thickness is about 30 microns, and in some more particular embodiment the central thickness is about 32 microns. In some embodiments the inlay has an edge thickness of about 3 microns to about 16 microns, and in some particular embodiments the edge thickness is about 12 microns. In some embodiments the anterior surface radius of curvature is about 7 mm to about 13 mm, and in some particular embodiments the anterior surface radius of curvature is about 10 mm. In some embodiments the posterior surface radius of curvature is about 5 mm to about 12 mm, and in some particular embodiments the posterior surface radius of curvature is about 8.5 mm.

Figure 7:
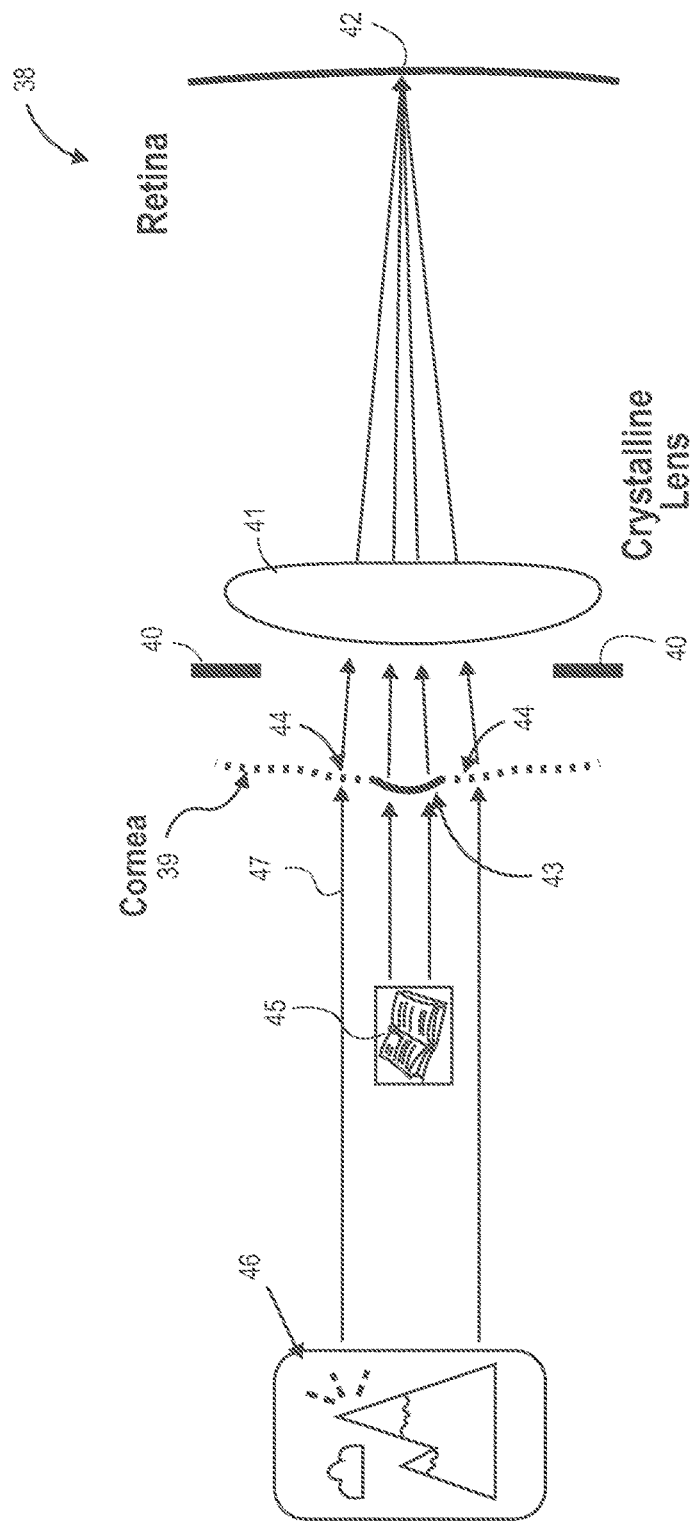
FIG. 7 is a diagram of an eye illustrating the use of a small diameter inlay to provide near vision according to an embodiment of the invention.

FIG. 7 shows an example of how a small inlay can provide near vision to a subject's eye while retaining some distance vision according to an embodiment of the invention. The eye 38 comprises the cornea 39, the pupil 40, the crystalline lens 41 and the retina 42. In this example, the small inlay (not shown) is implanted centrally in the cornea to create a small diameter "effect" zone 43. The small inlay has a smaller diameter than the pupil 40 so that the resulting "effect" zone 43 has a smaller diameter than the optical zone of the cornea. The "effect" zone 43 provides near vision by increasing the curvature of the anterior corneal surface, and therefore the diopter power within the "effect" zone 43. The region 44 of the cornea peripheral to the "effect" zone provides distance vision.

To increase the diopter power within the "effect" zone 43, the small inlay has a higher curvature than the pre-implant anterior corneal surface to increase the curvature of the anterior corneal surface within the "effect" zone 43. The inlay may further increase the diopter power within the "effect" zone 43 by having an index of refraction that is higher than the index of refraction of the cornea ($n_{cornea}$=1.376). Thus, the increase in the diopter power within the "effect" zone 43 may be due to the change in the anterior corneal surface induced by the inlay or a combination of the change in the anterior cornea surface and the index of refraction of the inlay. For early presbyopes (e.g., about 45 to 55 years of age), at least 1 diopter is typically required for near vision. For complete presbyopes (e.g., about 60 years of age or older), between 2 and 3 diopters of additional power is required.

An advantage of the small intracorneal inlay is that when concentrating on nearby objects 45, the pupil naturally becomes smaller (e.g., near point miosis) making the inlay effect even more effective. Further increases in the inlay effect can be achieved by simply increasing the illumination of a nearby object (e.g., turning up a reading light).

Because the inlay is smaller than the diameter of the pupil 40, light rays 47 from distant objects 46 by-pass the inlay and refract using the region of the cornea peripheral to the "effect" zone to create an image of the distant objects on the retina 42, as shown in FIG. 7. This is particularly true with larger pupils. At night, when distance vision is most important, the pupil naturally becomes larger, thereby reducing the inlay effect and maximizing distance vision.

TABLE 1

Examples of Ideal Anterior Corneal Surface Change Designs

| Design Type (mm) | Pupil Size | ADD (diopters) | "hctr" (microns) | rad zone (mm) | a6 ($mm^{-5}$) | a8 ($mm^{-7}$) |
|---|---|---|---|---|---|---|
| MaxN @ 2.5 | small | 1.5 | 4.30 | 1.39 | −4.500E−04 | 2.800E−04 |
| MaxN @ 3.0 | nominal | 1.5 | 5.06 | 1.50 | −2.830E−04 | 1.466E−04 |
| MaxN @ 3.5 | large | 1.5 | 6.24 | 1.66 | −3.374E−04 | 9.972E−05 |
| MaxN @ 2.5 | small | 2.0 | 5.38 | 1.36 | −2.450E−03 | 8.100E−04 |

TABLE 1-continued

Examples of Ideal Anterior Corneal Surface Change Designs

| Design Type | Pupil Size | ADD (diopters) | "hctr" (microns) | rad zone (mm) | a6 (mm$^{-5}$) | a8 (mm$^{-7}$) |
|---|---|---|---|---|---|---|
| MaxN @ 3.0 | nominal | 2.0 | 7.15 | 1.55 | −1.830E−03 | 4.420E−04 |
| MaxN @ 3.5 | large | 2.0 | 10.70 | 1.87 | −6.014E−04 | 1.108E−04 |
| MaxN @ 2.5 | small | 2.5 | 6.58 | 1.38 | −2.247E−03 | 7.904E−04 |
| MaxN @ 3.0 | nominal | 2.5 | 9.87 | 1.68 | −7.639E−04 | 1.950E−04 |
| MaxN @ 3.5 | large | 2.5 | 13.70 | 1.97 | −3.658E−04 | 7.109E−05 |

TABLE 2

Individual Subject Scaling Factors and Base Fit Parameters

|  | Verticle | Horizontal | % Fit |
|---|---|---|---|
| 1 | 1.30 | 1.08 | 1.1% |
| 2 | 0.92 | 1.15 | 0.3% |
| 3 | 0.86 | 0.88 | 1.3% |
| 4 | 0.84 | 1.12 | 0.3% |
| 5 | 1.46 | 0.99 | 1.7% |
| 6 | 1.40 | 0.82 | 1.9% |
| 7 | 1.35 | 0.96 | 0.8% |
| 8 | 0.83 | 0.92 | 1.0% |
| 9 | 0.91 | 0.91 | 1.9% |
| 10 | 1.20 | 1.01 | 0.7% |
| 11 | 0.96 | 1.14 | 0.4% |
| 12 | 1.12 | 0.85 | 2.3% |
| 13 | 1.22 | 0.88 | 1.2% |
| 14 | 1.17 | 1.02 | 0.4% |
| 15 | 0.85 | 0.91 | 2.6% |
| 16 | 0.63 | 1.09 | 0.4% |
| 17 | 0.86 | 1.19 | 1.9% |
| 18 | 1.30 | 0.76 | 3.3% |
| 19 | 1.31 | 0.95 | 0.7% |
| 20 | 1.01 | 1.00 | 1.1% |
| 21 | 1.21 | 1.00 | 0.2% |
| 22 | 0.92 | 1.07 | 0.7% |
| 23 | 1.07 | 0.81 | 1.4% |
| 24 | 0.74 | 0.89 | 5.1% |
| 25 | 0.98 | 1.00 | 0.3% |
| 26 | 1.01 | 1.17 | 1.5% |
| 27 | 1.12 | 0.94 | 1.5% |
| 28 | 0.80 | 0.94 | 0.3% |
| 29 | 0.67 | 0.87 | 1.3% |
| 30 | 1.71 | 0.66 | 2.7% |
| 31 | 0.68 | 1.06 | 0.1% |

| Best Shape | (microns) |
|---|---|
| a0 | 7.6200 |
| a2 | −5.5276 |
| a4 | 1.4694 |
| a6 | −0.1695 |
| a8 | 0.0072 |

What is claimed is:

1. A method of treatment for presbyopia of an eye, comprising:
   positioning a corneal inlay within the cornea, the corneal inlay having a diameter of about 1 mm to about 3 mm and smaller than a diameter of a pupil of the eye, the corneal inlay having an anterior surface comprising a corrective portion with a single radius of curvature, the corrective portion including an apex of the anterior surface; and
   altering a shape of an anterior surface of a cornea with the corneal inlay, the altered shape including a central near region for near vision and an intermediate region for intermediate vision that is peripheral to the central near region; and
   maintaining distance vision in a peripheral region that is peripheral to the intermediate region,
   wherein altering the shape of the anterior surface of a cornea with the corneal inlay comprises creating a central elevation change, and wherein the corneal inlay has a central thickness that is 3-7 times the central elevation change.

2. The method of claim 1 wherein positioning a corneal inlay within the cornea comprises lifting a corneal flap, implanting the corneal inlay on exposed corneal tissue, and repositioning the corneal flap on top of the corneal inlay.

3. The method of claim 1 wherein the intermediate region has an outer diameter greater than the diameter of the corneal inlay.

4. The method of claim 1 wherein the positioning step comprises implanting the corneal inlay at a depth of approximately 250 microns or less deep in the cornea.

5. The method of claim 1 further comprising, prior to altering the shape on the anterior surface of the cornea with the corneal inlay, performing a corrective procedure on the cornea.

6. The method of claim 5 wherein performing a corrective procedure on the cornea comprises performing a LASIK procedure on the cornea.

7. The method of claim 1 wherein the altering step further comprises increasing the curvature of the anterior surface of the cornea in the central near region.

8. The method of claim 1 wherein the positioning step further comprises positioning the corneal inlay within the cornea, the corneal inlay having a diameter of about 1 mm to about 2 mm and smaller than a measured diameter of a pupil of the eye.

9. The method of claim 1 wherein the positioning step further comprises positioning the corneal inlay having the diameter smaller than the diameter of the pupil to enable near vision and distance vision by the corrective portion with the single radius of curvature.

10. The method of claim 1 wherein the positioning step further comprises positioning the corneal inlay centrally in the cornea to create an effect zone smaller than the optical zone of the cornea.

11. The method of claim 9 wherein the positioning step further comprises positioning the corneal inlay having a higher curvature than the pre-implant anterior corneal surface to increase the curvature of the anterior corneal surface within the effect zone.

* * * * *